(12) United States Patent
Luo et al.

(10) Patent No.: US 10,555,797 B2
(45) Date of Patent: Feb. 11, 2020

(54) ELECTRIC TOOTHBRUSH HANDLE AND ELECTRIC TOOTHBRUSH

(71) Applicant: NINGBO SEAGO ELECTRIC CO., LTD, Ningbo (CN)

(72) Inventors: Ning Luo, Ningbo (CN); Yanzhong Cai, Leping (CN); Weibing Peng, Jiujiang (CN)

(*) Notice: Subject to any disclaimer, the term of this patent is extended or adjusted under 35 U.S.C. 154(b) by 349 days.

(21) Appl. No.: 15/374,005

(22) Filed: Dec. 9, 2016

(65) Prior Publication Data

US 2017/0360538 A1 Dec. 21, 2017

(30) Foreign Application Priority Data

Jun. 15, 2016 (CN) .......................... 2016 1 0422596

(51) Int. Cl.
| | | |
|---|---|---|
| *A61C 17/34* | (2006.01) | |
| *A46B 5/00* | (2006.01) | |
| *A61C 17/22* | (2006.01) | |
| *A46B 9/04* | (2006.01) | |
| *A46B 15/00* | (2006.01) | |

(52) U.S. Cl.
CPC .......... *A61C 17/221* (2013.01); *A46B 5/0095* (2013.01); *A46B 9/04* (2013.01); *A46B 15/0036* (2013.01); *A61C 17/225* (2013.01); *A61C 17/3409* (2013.01)

(58) Field of Classification Search
CPC ........ A46B 15/0036; A46B 2200/1066; A46B 5/00; A46B 5/02; A61C 17/34
USPC ............................... 15/22.1, 105, 106, 167.1
See application file for complete search history.

(56) References Cited

U.S. PATENT DOCUMENTS

2010/0024143 A1* 2/2010 Dickie .................... A46B 5/00
15/167.1
2014/0007361 A1* 1/2014 Nazaroff ............ A46B 15/0044
15/22.1

* cited by examiner

*Primary Examiner* — Michael D Jennings
(74) *Attorney, Agent, or Firm* — Schmeiser, Olsen & Watts LLP

(57) ABSTRACT

The invention relates to an electric toothbrush handle and an electric toothbrush. The electric toothbrush handle comprises: a shell in the inner cavity of which at least one light emitting element is arranged; and a display interface arranged on the outer side of the shell and covering the light emitting element; wherein the display interface is provided with a mark in a set shape at a position corresponding to each light emitting element; the light of the light emitting element is capable of penetrating through the display interface so that the mark is visible. With the mark formed on the display interface, the machining process of the electric toothbrush handle is simplified, and the electric toothbrush with the electric toothbrush handle can effectively prevent water ingress.

16 Claims, 6 Drawing Sheets

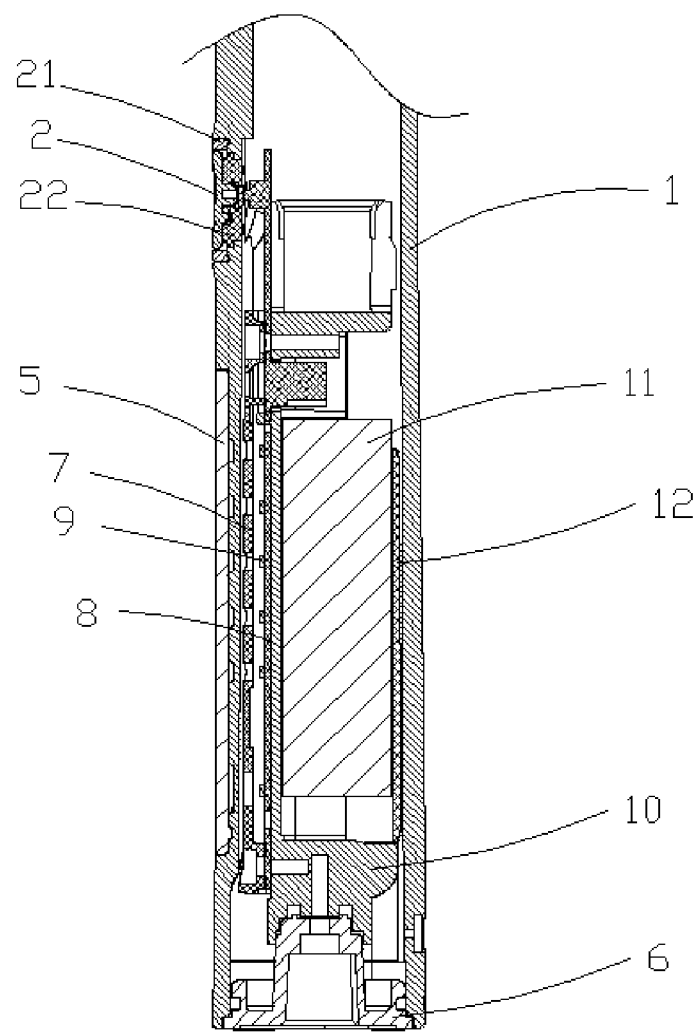
Fig. 4-a
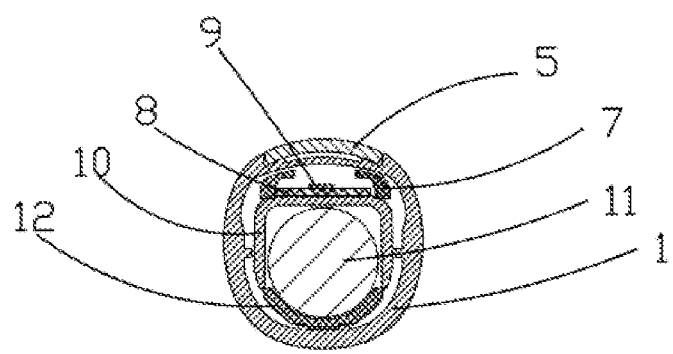
Fig. 4-b

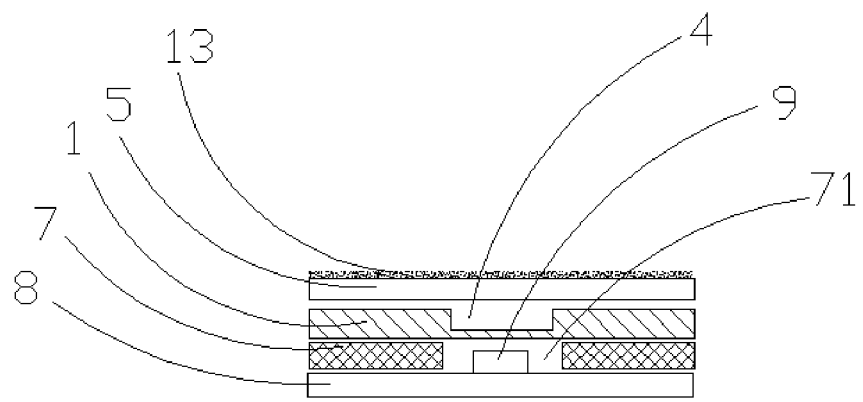
Fig. 5-a
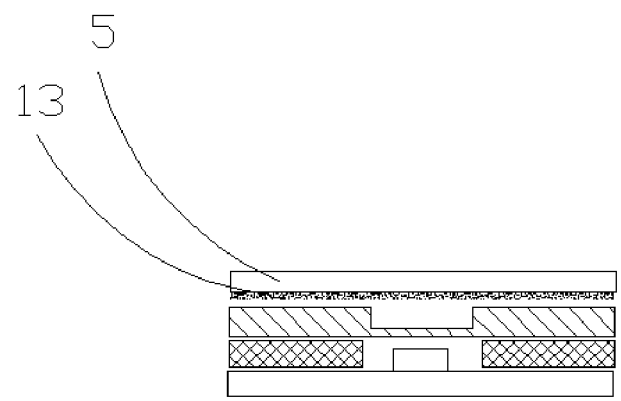
Fig. 5-b

ELECTRIC TOOTHBRUSH HANDLE AND ELECTRIC TOOTHBRUSH

FIELD OF THE INVENTION

The present invention relates to the field of oral health, and particularly relates to an electric toothbrush handle and an electric toothbrush.

BACKGROUND OF THE INVENTION

An electric toothbrush serves as a personal care appliance in the field of oral health, and the brush head vibrates at a high frequency via quick rotation or vibration of an electric movement, decomposes toothpaste into superfine foams and then cleans teeth deeply. Compared with a common toothbrush, the electric toothbrush has the advantages of clearing dental plaque more thoroughly as well as reducing oral diseases including gingivitis, periodontal disease, gingival bleeding and the like more scientifically and effectively, and thus is gradually favored by consumers.

With respect to its structure, the electric toothbrush is mostly provided with a user interface on the surface, and the user interface is mainly used for displaying information indication associated with the operating mode of the toothbrush. For example, the operating mode can be current clean degree, and the associated information indication can be brush head speed (or speed change rule), cleaning time and the like under the clean degree.

User interfaces mainly include visible interfaces and invisible interfaces, wherein in most of the visible interfaces, the handle is provided with a hole, and then information is displayed to a user in a light guide manner of a transparent part installed on the hole; in consideration of the water environment of the toothbrush in use, the visible interfaces mostly have the defect of water leak; and in the invisible user interfaces, a coating is generally arranged on one side of the transparent handle, and the coating is mostly a composite layer, leading to the drawbacks of high cost and complex process.

SUMMARY OF THE INVENTION

Technical Problem

In view of this, the technical problem to be solved by the present invention is how to effectively avoid the possible problem of water ingress when an electric toothbrush is in a water environment while the process of the structure related to the display function of an electric toothbrush handle is simplified.

Solution

In order to solve the above technical problem, according to one embodiment of the present invention, provided is an electric toothbrush handle, including:
a shell, wherein at least one light emitting element is arranged in the inner cavity of the shell; and
a display interface, which is arranged on the outer side of the shell and covers the light emitting element;
wherein the display interface is provided with a mark in a set shape at a position corresponding to each light emitting element; and
the light of the light emitting element is capable of penetrating through the display interface so that the mark is visible.

For the above electric toothbrush handle, in one possible implementation, the shell is provided with a blind hole corresponding to each light emitting element; and
the light of the light emitting element penetrates through the bottom thickness of the blind hole and impinges on the corresponding mark of the display interface.

For the above electric toothbrush handle, in one possible implementation, the electric toothbrush handle further includes a shading part, which is provided with a light transmission structure corresponding to the light emitting element; and
the light of the light emitting element successively penetrates through the corresponding light transmission structure and the bottom thickness of the blind hole and impinges on the corresponding mark.

For the above electric toothbrush handle, in one possible implementation, an installation groove is machined on the outer surface of the shell; and
the installation groove is provided with the blind hole at the position corresponding to the light emitting element;
wherein the display interface can be installed on the outer surface of the shell via the installation groove in a matching manner.

For the above electric toothbrush handle, in one possible implementation, the display interface is of a transparent structure.

For the above electric toothbrush handle, in one possible implementation, the mark is of a nontransparent layer structure.

For the above electric toothbrush handle, in one possible implementation, a driving control part is also arranged in the shell, and includes:
a motor, with a power output end connected with a brush head installed on the electric toothbrush handle, and used for driving the brush head into motion; and
a control panel, used for controlling the motor and the light emitting element.

For the above electric toothbrush handle, in one possible implementation, the light emitting element and the shading part are both fixed on the control panel.

For the above electric toothbrush handle, in one possible implementation, at least one switch for selecting a target working mode is also arranged on the shell, and the switch is electrically connected with the control panel.

For the above electric toothbrush handle, in one possible implementation, the bottom thickness of the blind hole is 0.3-1 mm.

In order to solve the above technical problem, according to another embodiment of the present invention, provided is an electric toothbrush, including an electric toothbrush handle and at least one brush head which can be installed at one end of the electric toothbrush handle, and the electric toothbrush handle is the aforementioned one.

Beneficial Effects

The process of making the mark (e.g., characters or literal information) of the display interface of the electric toothbrush handle in the embodiment of the present invention is simple, and a coating for forming the mark can be selectively arranged on the outer side or the inner side of the panel according to practical situation, so the design is flexible, and the formed mark is not prone to damage.

In the case of the electric toothbrush with the electric toothbrush handle, wall thinning processing is performed on the shell of the electric toothbrush handle, so that the light of the light emitting element can penetrate to the mark on a certain side of the display interface of the electric toothbrush handle to realize visualization, a hole at the installation position (i.e., the installation groove) of the display interface is not needed, and thus the water ingress phenomenon of the electric toothbrush is avoided.

Other features and aspects of the present invention will become apparent from the following detailed description of the exemplary embodiments with reference to the accompanying drawings.

BRIEF DESCRIPTION OF THE DRAWINGS

The accompanying drawings included in the specification and constituting a part of the specification, together with the specification, illustrate the exemplary embodiments, features and aspects of the present invention, and are used for interpreting the principle of the present invention.

FIG. 4-*a* shows a sectional schematic diagram I of the electric toothbrush handle in one embodiment of the present invention (in the axial direction);

FIG. 4-*b* shows a sectional schematic diagram II of the electric toothbrush handle in one embodiment of the present invention (in the radial direction);

FIG. 5-*a* shows a schematic diagram I of the coating of the electric toothbrush handle in one embodiment of the present invention (the coating is arranged on the outer side of the display interface);

FIG. 5-*b* shows a schematic diagram II of the coating of the electric toothbrush handle in one embodiment of the present invention (the coating is arranged on the inner side of the display interface);

Figure 1:
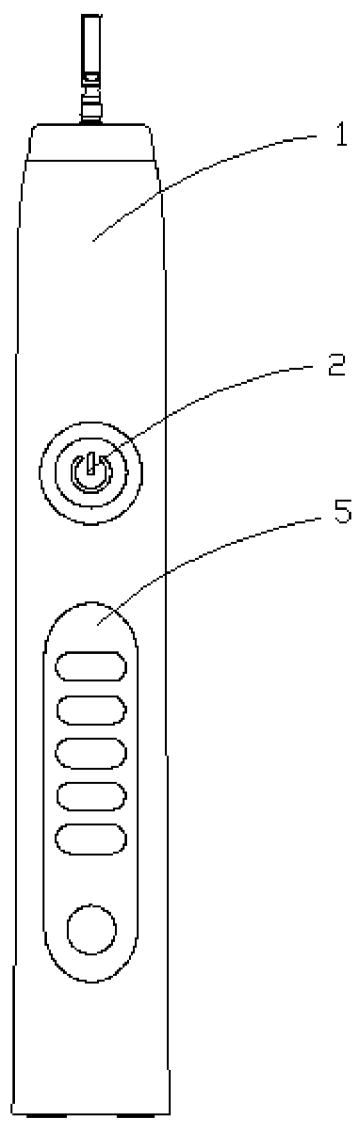
FIG. 1 shows a schematic structural diagram of an electric toothbrush handle in one embodiment of the present invention.

LIST OF REFERENCE SIGNS 1, shell
2, button
21, button ring
22, soft rubber
3, installation groove
4, blind hole
5, display interface
6, bottom cover
7, shading part
71, light transmission structure
8, control panel
9, light emitting element
10, support
11, battery
12, battery cover
13, coating
601, handle area
602, display area
603, button area

DETAILED DESCRIPTION OF THE EMBODIMENTS

Various exemplary embodiments, features and aspects of the present invention will be described in detail below with reference to the accompanying drawings. The same signs in the drawings represent elements with the same or similar functions. Although various aspects of the embodiments are illustrated in the drawings, the drawings do not need to be drawn to scale unless otherwise indicated.

The special word "exemplary" herein means "using as an example or an embodiment or illustrative". Any "exemplary" embodiment described herein should not be interpreted as being superior to or better than other embodiments.

In addition, numerous specific details are given in the specific embodiments below in order to better illustrate the present invention. Those skilled in the art should understand that the present invention can also be implemented without some specific details. In some embodiments, the methods, means and circuits well known to those skilled in the art are not described in detail, thereby highlighting the theme of the present invention.

Embodiment 1

Figure 2:
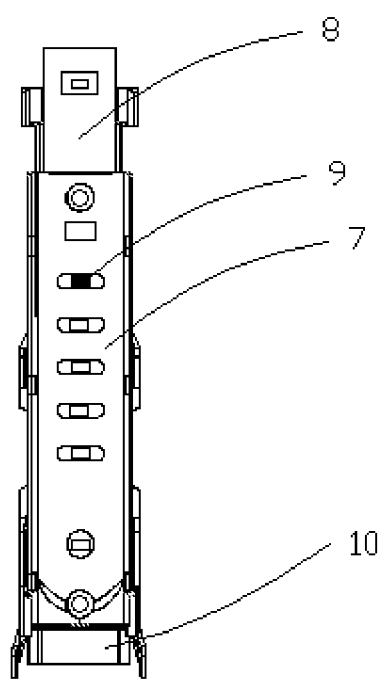
FIG. 2 shows a schematic diagram of internal components of the electric toothbrush handle in one embodiment of the present invention.
Figure 3:
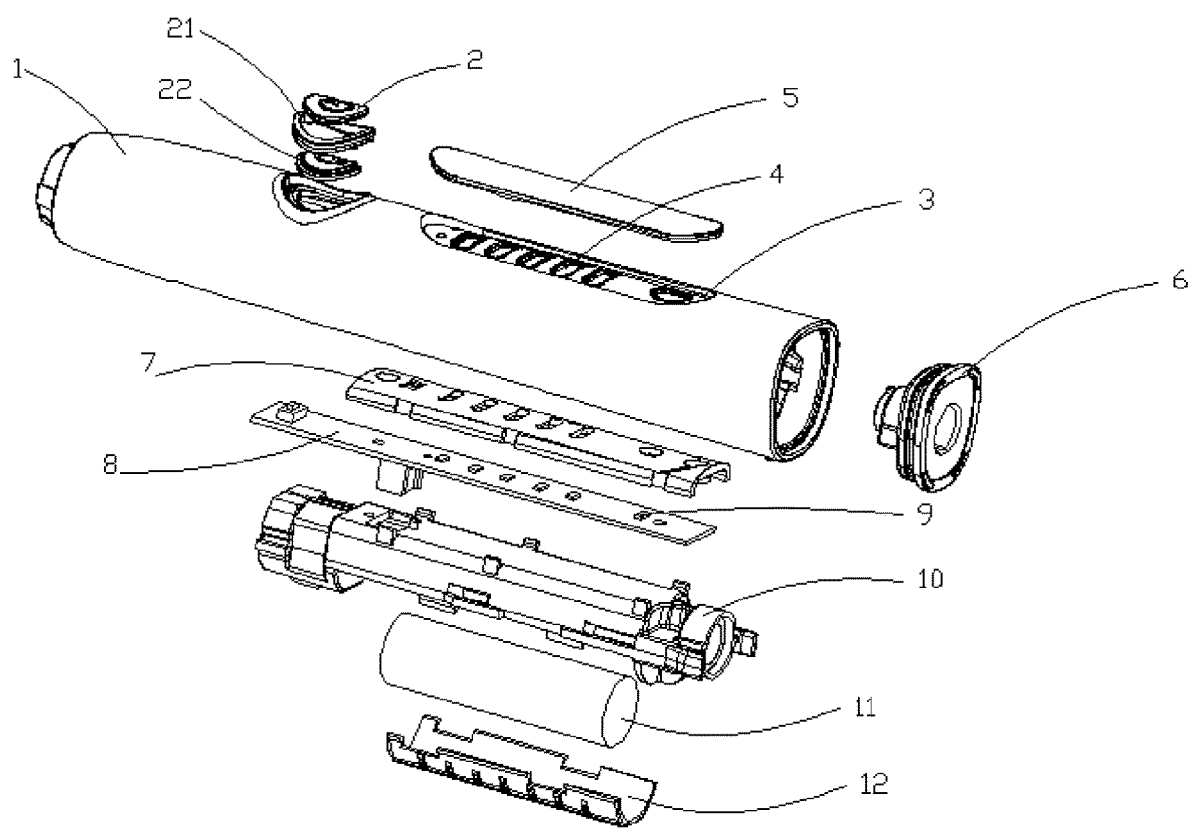
FIG. 3 shows an exploded schematic diagram during assembly of FIG. 1 and FIG. 2.

FIG. 1 shows a schematic structural diagram of an electric toothbrush handle in one embodiment of the present invention. FIG. 2 shows a schematic structural diagram of internal components of the electric toothbrush handle in one embodiment of the present invention. FIG. 3 shows an exploded view of the electric toothbrush handle of FIG. 1 and FIG. 2 after assembly.

As shown in FIG. 1, the electric toothbrush handle mainly includes:

a shell 1, wherein at least one light emitting element 9 is arranged in the inner cavity of the shell 1; and a display interface 5, which is arranged on the outer side of the shell 1 and covers the light emitting element 9;

wherein the display interface 5 is provided with a mark in a set shape at a position corresponding to each light emitting element 9; and the light of the light emitting element 9 is capable of penetrating through the display interface 5 so that the mark is visible.

In one possible implementation, the shell 1 may be of a light tight structure (e.g., a nontransparent structure), and the nontransparent structure is provided with a blind hole 4 corresponding to the light emitting element 9. In this case, the light tight shell 1 has light transmission performance at the bottom thickness of the blind hole 4 by thinning the shell 1, and the light of the light emitting element 9 penetrates through the bottom thickness of the blind hole 4 and impinges on the mark of the display interface 5. Preferably, the bottom thickness of the blind hole is 0.3-1 mm. By thinning the shell 1, not only can the light of each light emitting element penetrate through the shell 1, but also water can be effectively prevented from entering the cavity of the shell 1 due to a closed structure of the shell 1. Of course, the shell 1 may also be of a light transmission structure, e.g., a transparent structure or a semitransparent structure, in this case, even if the shell 1 is not thinned, the light of the light emitting element 9 can penetrate through the shell 1 and impinge on the display interface 5. In this case, the internal components are visible.

As shown in FIG. 3, in one possible implementation, the display interface 5 and the shell 1 can be assembled in the following manner.

An installation groove 3 is dug in the outer surface of the shell 1, the display interface 5 can be installed (e.g., buckled) on the outer surface of the shell 1 via the installation groove 3 in a matching manner, and the aforementioned blind hole 4 is machined in the installation groove 3 at a position corresponding to the light emitting element 9.

In one possible implementation, the display interface 5 is of a light transmission structure (e.g., a transparent structure), the mark is of a light tight structure (e.g., a nontransparent layer structure), and the light emitting element 9 may be an LED lamp. That is, the light emitted by the LED lamp can impinge on the marks on one side of the display interface 5 after penetrating through the bottom thickness of the blind hole 4 in the shell 1.

FIG. 4-a and FIG. 4-b respectively show sectional schematic diagrams of the electric toothbrush handle in the axial direction and the radial direction. FIG. 5-a and FIG. 5-b respectively show position relation diagrams of the mark of the electric toothbrush handle relative to the display interface 5.

The internal components arranged in the inner cavity of the shell 1 mainly include a driving control part which is mainly used for driving a brush head connected with it to act; the driving control part includes:

a motor, with a power output end extending out of the front end of the electric toothbrush handle and connected with the brush head, and used for driving the brush head to swing; and a control panel 8, used for controlling the action parameters of the motor, and enabling the aforementioned display interface 5 to give indication information for characterizing a target working mode, that is, visualizing the mark corresponding to the target working mode by lightening the corresponding light emitting element 9.

Specifically:

The electric toothbrush handle is provided with at least one switch (e.g., which may be a button 2 for pressing operation), and the button 2 is electrically connected with the control panel 8 and is used for triggering the control panel 8 to emit an instruction of selecting one of a plurality of working modes as a target working mode, or an instruction of switching from the current working mode to the target working mode; according to the instruction, on the one hand, the motor responds to the instruction of the control panel 8 to drive the brush head to accomplish a series of motion (e.g., vibration) adapted to the target working mode according to set control parameters and/or a parameter group, and on the other hand, the corresponding light emitting element 9 is lightened, and the mark of the display interface 5 transmits indication information (e.g., mode mark, motion parameter of the brush head, etc.) to a user.

The internal components further include:

a power supply, which can supply power to the light emitting element 9, so that the light emitting element 9 emits light to realize the display function of the handle. The power supply can also supply power to the driving control part, so as to drive the brush head into motion. The power supply can be realized in various ways, can be various types of batteries or transformers or the like, and can be flexibly selected according to actual application requirements.

For example, in one possible implementation, the power supply is a battery 11. In this case, one side of a support 10 also serving as an internal component is matched with a battery cover 12 to form an installation space of the battery 11.

The control panel 8 is fixed on the other side (i.e., the side close to the display interface 5) of the support 10.

Moreover, the tail end of the support 10 axially limits the internal components via a bottom cover 6 arranged at the rear end of the shell 1.

In a specific implementation, the aforementioned light emitting element 9 is fixed on one side of the control panel 8 close to the display interface 5, a shading part 7 is also arranged on the side of the control panel 8 at a position corresponding to the light emitting element 9, the shading part 7 is provided with corresponding light transmission structures 71, e.g., a round hole close to the rear end of the electric toothbrush handle and a strip hole in front of the round holes in FIG. 2, and the light transmission structures 71 are mainly used for limiting the light of each light emitting element 9 to the mark associated therewith on the display interface 5. In this case, the light emitted by the light emitting element 9 successively penetrates through the light transmission structures 71 on the shading part 7 and the blind holes 4 of the electric toothbrush handle and then arrives at the mark of the display interface 5 to lighten it, thereby realizing visualization.

It should be noted that although the electric toothbrush handle is introduced above taking the panel-type display interface 5 and the shading part 7 shown in the figures as an example, those skilled in the art could understand that the present invention should not be limited thereto. In fact, a user completely can flexibly set the specific shapes of the display interface 5, the shading part 7 and the light transmission structures 71 according to personal preference and/or practical application scenarios, as long as the light transmission performance and the accuracy of the light path are guaranteed.

As mentioned above, the display interface 5 in the present invention is of a structure adapted to the installation groove 3 of the shell 1, a nontransparent coating 13 can be arranged (e.g., sprayed or pasted) on the outer side (FIG. 5-a) or the inner side (FIG. 5-b) (the side close to the shading part 7) of the display interface 5 according to practical product demands and forms, then the coating 13 is peeled off according to a set shape in a laser engraving manner, and the positions of the peeled shapes correspond to the aforementioned light emitting element 9 and the corresponding light transmission structures 71 on the shading part 7 one by one.

Thus, when the electric toothbrush is in the target working mode via the button 2, the light emitted by the corresponding light emitting element 9 penetrates through the light transmission structures 71 to lighten the mark in the set shape on one side of the display interface 5 accurately and reliably in the target working mode, and the mark is formed on the display interface 5 instead of the shell 1, so the process is simplified; and the shape of the mark can be flexibly adjusted in the laser engraving manner.

Embodiment 2

Figure 6:
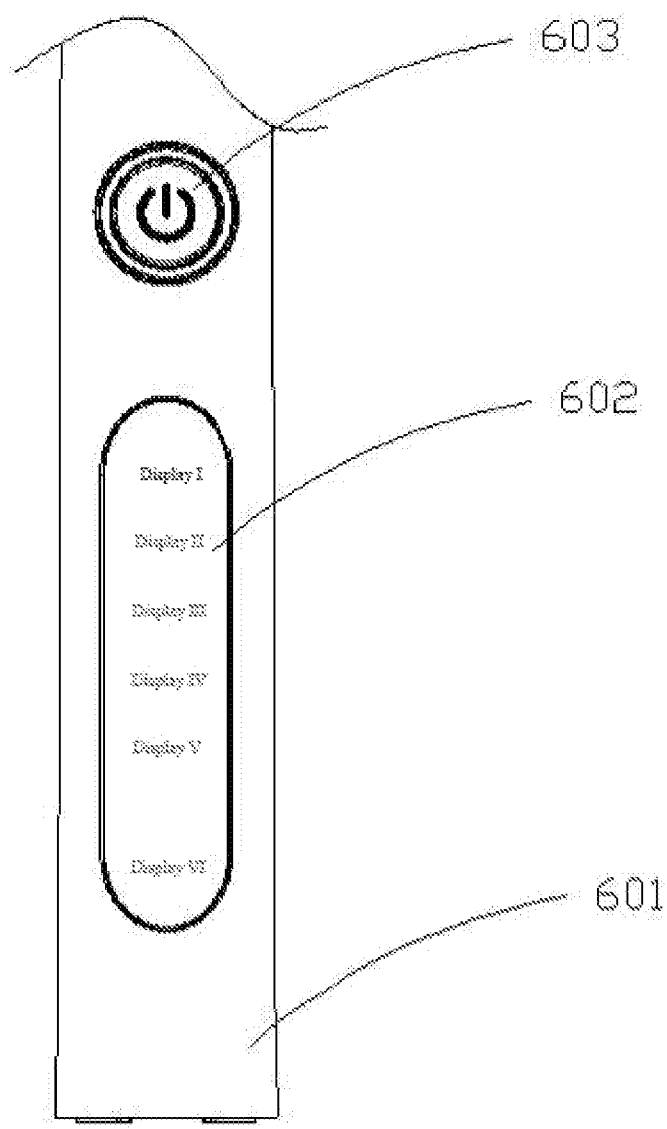
FIG. 6 shows an application schematic diagram of an electric toothbrush in another embodiment of the present invention.

FIG. 6 shows another embodiment of the present invention, that is, a schematic diagram of an application structure of an electric toothbrush with the aforementioned electric toothbrush handle. In a specific application example, the electric toothbrush mainly includes a handle area 601, a display area 602 and a button area 603.

The electric toothbrush mainly includes the aforementioned electric toothbrush handle and at least one brush head which can be installed at one end of the electric toothbrush handle, e.g., may have a multi-brush-head replaceable structure. The brush head is mainly used for cleaning the teeth of a user. The brush head can also be used for cleaning other oral parts such as tongue and the like according to personal use habit and the specific design of the brush head, or other reasonable parts in non-oral environments, of course.

The handle area 601 is provided with a corresponding hole for installing the button 2; in order to improve the sealing performance at the hole, further referring to FIG. 3, a button ring 21 is arranged at the inner edge of the hole, so that the outer edge (in the circumferential direction) of the button 2 is in tight contact with the button ring 21; and a buffer washer (e.g., soft rubber 22) is arranged between the button 2 and the hole, so that when the button 2 is pressed, the outer edge of the inner side of its end face is tightly attached to the soft rubber 22, and its middle part is reliably jointed with the control panel 8.

Moreover, in order to further improve the joint reliability between the button 2 and the control panel 8 when the button is pressed, further referring to FIG. 4-a, a protrusion can be machined on the inner side of the end face of the button 2, and a recess corresponding to the protrusion can be formed on the soft rubber 22.

Described above are merely the specific embodiments of the present invention, but the protection scope of the present invention is not limited to this. Any variations or substitutions within the disclosed technical scope of the present invention that are readily conceivable to those skilled in the art shall fall within the protection scope of the present invention. Thus, the protection scope of the present invention shall be defined by the protection scope of the claims.

The invention claimed is:

1. An electric toothbrush handle, comprising:
    a shell, wherein at least one light emitting element is arranged in an inner cavity of the shell; and
    a display interface, which is arranged on an outer side of the shell and covers the light emitting element;
    wherein the display interface is provided with a mark in a set shape at a position corresponding to each light emitting element;
    the light of the light emitting element is capable of penetrating through the display interface so that the mark is visible;
    an installation groove is machined on an outer surface of the shell, the installation groove is recessed from the outer surface of the shell which is away from an interior of the handle towards an inner surface of the shell which is close to the interior of the handle, and the display interface is installed on the outer surface of the shell via the installation groove in a matching manner,
    the shell is provided with a blind hole on the installation groove of the shell corresponding to each light emitting element, wherein the blind hole is formed in a body of the shell from an surface of the installation groove which houses the display interface towards the interior of the handle, the blind hole is recessed from the outer surface of the shell towards the inner surface of the shell, and the blind hole has a bottom thickness in the body of the shell on a side of the inner surface of the shell; and
    the light of the light emitting element penetrates through the bottom thickness of the blind hole and impinges on the corresponding mark of the display interface.

2. The electric toothbrush handle of claim 1, wherein the electric toothbrush handle further comprises a shading part, which is provided with a light transmission structure corresponding to the light emitting element; and
    the light of the light emitting element successively penetrates through the corresponding light transmission structure and then through the bottom thickness of the blind hole and then impinges on the corresponding mark.

3. The electric toothbrush handle of claim 2, wherein a driving control part is also arranged in the shell, and comprises:
    a motor, with a power output end connected with a brush head installed on the electric toothbrush handle, and used for driving the brush head into motion; and
    a control panel, used for controlling the motor and the light emitting element.

4. The electric toothbrush handle of claim 3, wherein the light emitting element and the shading part are both fixed on the control panel.

5. The electric toothbrush handle of claim 3, wherein at least one switch for selecting a target working mode is also arranged on the shell, and the switch is electrically connected with the control panel.

6. The electric toothbrush handle of claim 1, wherein the display interface is of a transparent structure.

7. The electric toothbrush handle of claim 1, wherein the mark is of a nontransparent layer structure.

8. The electric toothbrush handle of claim 1, wherein the bottom thickness of the blind hole is 0.3-1 mm.

9. An electric toothbrush, comprising an electric toothbrush handle and at least one brush head which can be installed at one end of the electric toothbrush handle, wherein the electric toothbrush handle comprising:
    a shell, wherein at least one light emitting element is arranged in an inner cavity of the shell; and
    a display interface, which is arranged on an outer side of the shell and covers the light emitting element;
    wherein the display interface is provided with a mark in a set shape at a position corresponding to each light emitting element;
    the light of the light emitting element is capable of penetrating through the display interface so that the mark is visible;
    an installation groove is machined on an outer surface of the shell, the installation groove is recessed from the outer surface of the shell which is away from an interior of the handle towards an inner surface of the shell which is close to the interior of the handle, and the display interface is installed on the outer surface of the shell via the installation groove in a matching manner,
    the shell is provided with a blind hole of the shell on the installation groove corresponding to each light emitting element, wherein the blind hole is forted in a body of the shell from an surface of the installation groove which houses the display interface towards the interior of the handle, the blind hole is recessed from the outer surface of the shell towards the inner surface of the shell, and the blind hole has a bottom thickness in the body of the shell on a side of the inner surface of the shell; and
    the light of the light emitting element penetrates through a bottom thickness of the blind hole and impinges on the corresponding mark of the display interface.

10. The electric toothbrush of claim 9, wherein the electric toothbrush handle further comprises a shading part, which is provided with a light transmission structure corresponding to the light emitting element; and
    the light of the light emitting element successively penetrates through the corresponding light transmission structure and the bottom thickness of the blind hole and impinges on the corresponding mark.

11. The electric toothbrush of claim 10, wherein a driving control part s also arranged in the shell, and comprises:

a motor, with a power output end connected with a brush head installed on the electric toothbrush handle, and used for driving the brush head into motion; and a control panel, used for controlling the motor and the light emitting element.

12. The electric toothbrush of claim 11, wherein the light emitting element and the shading part are both fixed on the control panel.

13. The electric toothbrush of claim 11, wherein at least one switch for selecting a target working mode is also arranged on the shell, and the switch is electrically connected with the control panel.

14. The c toothbrush of claim 9, wherein the display interface is of a transparent structure.

15. The electric toothbrush of claim 9, wherein the mark is of a nontransparent layer structure.

16. The electric toothbrush of claim 9, wherein the bottom thickness of the blind hole is 0.3-1 mm.

* * * * *